US008155993B2

(12) United States Patent
de Nijs et al.

(10) Patent No.: US 8,155,993 B2
(45) Date of Patent: Apr. 10, 2012

(54) APPARATUS AND METHODS FOR ASSESSING A PHARMACEUTICAL PRODUCT

(75) Inventors: Paul Leonce Irma de Nijs, Kasterlee (BE); Gilbertus Johannes Martinus Verkuijlen, Eindhoven (NL)

(73) Assignee: Janssen Pharmaceutica, N.V., Beerse (BE)

( * ) Notice: Subject to any disclaimer, the term of this patent is extended or adjusted under 35 U.S.C. 154(b) by 1880 days.

(21) Appl. No.: 10/868,739

(22) Filed: Jun. 15, 2004

(65) Prior Publication Data

US 2005/0278185 A1    Dec. 15, 2005

(51) Int. Cl.
*G06Q 10/00* (2012.01)
(52) U.S. Cl. ............... 705/7.35; 705/7.41; 705/7.29
(58) Field of Classification Search .................. None
See application file for complete search history.

(56) References Cited

U.S. PATENT DOCUMENTS

| | | | | |
|---|---|---|---|---|
| 5,731,991 A | * | 3/1998 | Kinra et al. | 702/186 |
| 5,872,850 A | * | 2/1999 | Klein et al. | 705/51 |
| 6,115,694 A | * | 9/2000 | Cheetham et al. | 705/10 |
| 6,236,990 B1 | * | 5/2001 | Geller et al. | 1/1 |
| 7,092,918 B1 | * | 8/2006 | Delurgio et al. | 705/400 |
| 7,099,857 B2 | * | 8/2006 | Lambert | 706/55 |
| 7,103,567 B2 | * | 9/2006 | Smukowski | 705/26 |
| 2001/0032196 A1 | * | 10/2001 | Krespi | 705/400 |
| 2002/0081750 A1 | * | 6/2002 | Ernest et al. | 436/518 |
| 2002/0087388 A1 | | 7/2002 | Keil et al. | |
| 2002/0184072 A1 | * | 12/2002 | Linde et al. | 705/10 |
| 2003/0061096 A1 | | 3/2003 | Gallivan et al. | |

FOREIGN PATENT DOCUMENTS

| | | |
|---|---|---|
| JP | 2003067489 | 3/2003 |
| WO | WO 0152126 A | 7/2001 |
| WO | WO 02054320 | 7/2002 |

OTHER PUBLICATIONS

Tarantino, David P. USing the Balanced Scorecard as a Performance Management Tool. The Physician Executive. Sep.-Oct. 2003.*
Fitzpatrick, Melissa A. Let's bring balance to health care. Nursing Management; Mar. 2002; 33, 3; ABI/INFORM Global p. 35.*
Automating the Balanced Scorecard. Corvu Managing business Performance. Apr. 1998. From www.corvu.com/papers/bsc.htm. Accessed using web.archive.org.*
Stonebraker JS (2002). How Bayer Makes Decisions to Develop New Drugs. INFORMS. 32(5): 77-90.*
Seget S (2003). Pharmaceutical Pricing Strategies. Reuters Business Insight Healthcare. Datamonitor PLC. 1-228.*
PriceIT InternationalTM data sheet. 2003. International Pricing Strategy. InPharmation.*
PriceIT InternationalTM data sheet. 2003. Your Products Price Sensitivity. InPharmation.*

(Continued)

*Primary Examiner* — Lynda Jasmin
*Assistant Examiner* — Brett Feeney
(74) *Attorney, Agent, or Firm* — Woodcock Washburn LLP

(57) ABSTRACT

A computer implemented tool for assisting in assessment of pharmaceutical products is provided. An input interface is adapted to accept a plurality of attribute descriptors relating to attributes of a product to be assessed, a plurality of attribute weights and a plurality of attribute scores. An assessment element combines the scores and weights to yield one or more assessment measures which are displayed using an output interface.

16 Claims, 10 Drawing Sheets

OTHER PUBLICATIONS

Perloff JM, Suslow VY and Suguin PJ (1996). Higher Prices from Entry: Pricing of Brand-Name Drugs. Department of Agricultural and Resource Economics, UCB, UC Berkeley. 1-40.*

Lu ZJ and Comanor WS (1998). Strategic Pricing of New Pharmaceuticals. The Review of Economic Statistics. 80(1): 108-118.*

Dean J (1969). Pricing Pioneering Products. The Journal of Industrial Economics. 17(3): 165-179.*

Vernon JA, Hughen WK and Johnson SJ (2005). Mathematical Modeling and Pharmaceutical Pricing: Analyses Used to Inform In-Licensing and Developmental Go/No-Go Decisions. Health Care Management Science 8:167-179.*

PriceIT™, Pharmaceutical Pricing Support System from Inpharmation Ltd., 1999-2000©, 38 pages.

English Translation of Japanese Patent Application No. 2007/515847: Final Rejection dated Sep. 28, 2010, 3 pages.

Japanese Patent Application No. 2007/515847: Final Rejection dated Sep. 28, 2010, 2 pages.

JP Application No. 2007-515847: Office Action (English Translation included) dated Oct. 5, 2010, 7 pages.

\* cited by examiner

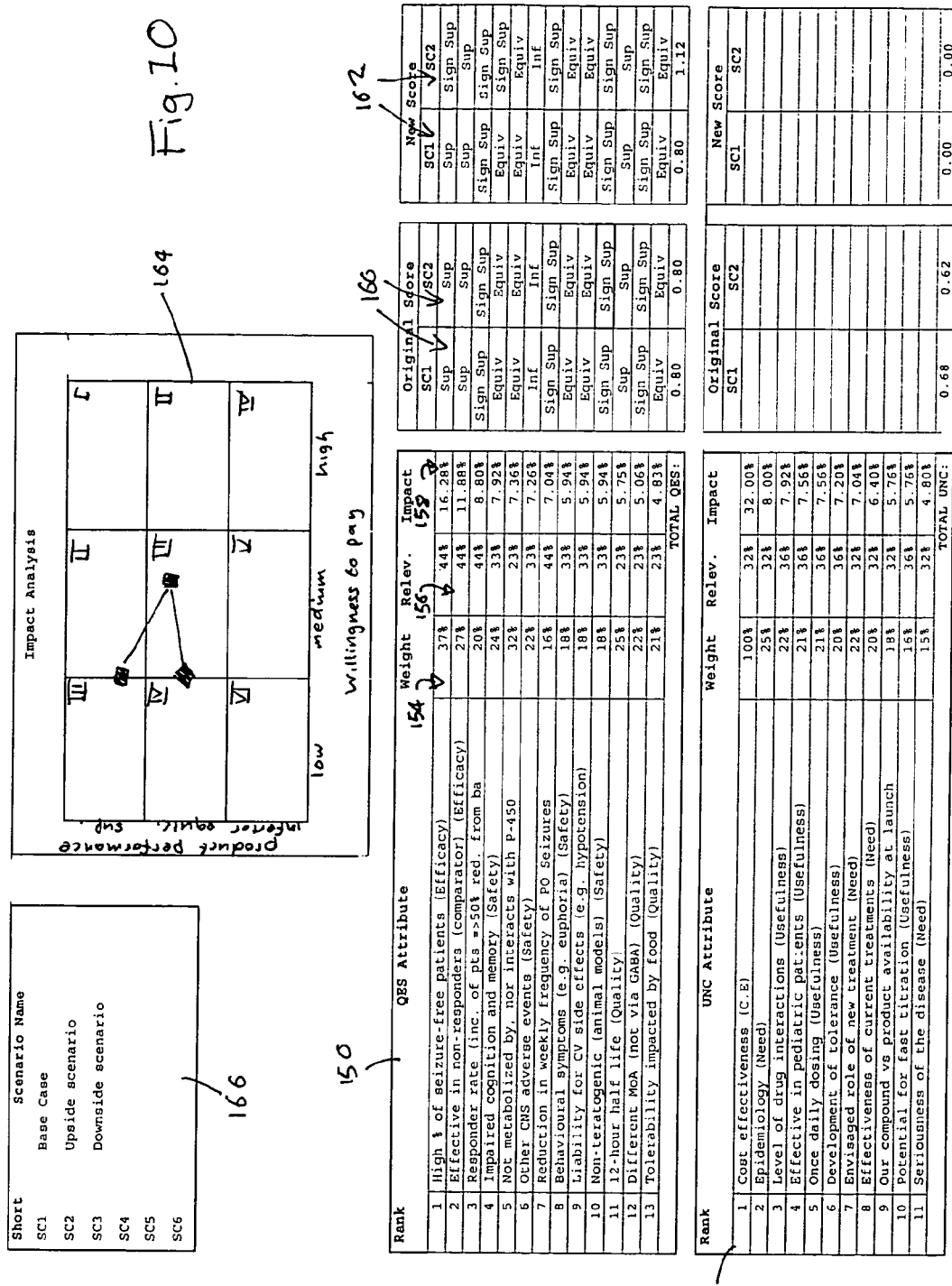

APPARATUS AND METHODS FOR ASSESSING A PHARMACEUTICAL PRODUCT

TECHNICAL FIELD

The invention relates to a method for computer assisted assessment of a pharmaceutical product.

The invention also relates to a computer system for assisting in and presenting results of an assessment of a pharmaceutical product.

The invention also relates to a method for combining scores from a plurality of assessment attributes to arrive at an overall assessment of a pharmaceutical product.

BACKGROUND OF THE INVENTION

In the pharmaceutical industry, there is a general need for systems and methods for evaluating the economic and clinical values and potentials of both new and established pharmaceutical compounds and other products. Such evaluations are required to estimate potential sales and suitable pricing levels, as well as to determine appropriate marketing strategies, or even whether to bring a product to a particular market at all.

Conventional marketing models frequently apply basic economic concepts such as supply and demand to make predictions of sales volumes for a product at particular price levels. Such models may take account of the market price for similar products, the size and flexibility of the target market, the effects of advertising spend on price and volume of sales, and relevant characteristics of markets in other countries.

The Price IT (RTM) product available from Inpharmation Ltd., Long Meadow, Spurgrove Lane, Frieth, Henley-on-Thames, England is a computer software package which includes eight different models to predict price-volume curves for pharmaceutical products. The models include: an "Exclusion Model" to determine infeasible combinations of volumes and prices; a "Value in Use Model" using the quality adjusted life year concept; a "Judged Model for Payers" to account for various assessments of price resistance levels; a "User Attraction Model" to combine performance assessments across a range of attributes; a "References Model" to account for clinician thinking with reference to already familiar products; an "International Model" based on per capita pharmaceutical spending and the known price in a reference market; a "Dorfman Steiner Model" allowing for price and advertising elasticity; and a "Judged Model for Doctors" using extrapolation between points representing judgements of demand for the product at various prices. To use each model a number of parameters must be entered, such as estimated demand, price, curve parameters, weights given to various model aspects and so on. The Price IT (RTM) product provides a results tool for combining the price-volume curves from the various models, subject to chosen model weights.

Although the Price IT (RTM) package provides a wide range of models for pharmaceutical pricing assessments, each model is simple and relies on very few input parameters. In real life the factors which combine to effect pharmaceutical value and potential are far more numerous.

SUMMARY OF THE INVENTION

The invention addresses problems and limitations of the related prior art. In particular, it would be desirable to combine expert judgements from a range of different professionals, such as doctors, pharmacists, regulatory experts, pricing and health economics experts, market research and product strategy experts, to access the economic potential and clinical value of a pharmaceutical product, especially, but not exclusively, with a view to developing appropriate pricing and marketing strategies.

To this end, it would also be desirable to provide a method and system for combining a wide range of different factors into a single assessment process.

It would also be desirable to provide an improved way to present the results of such an assessment process.

The invention provides a tool for assisting in the assessment of a pharmaceutical product, comprising: an input interface adapted to accept a plurality of attribute descriptors relating to attributes of the product to be assessed, a plurality of attribute weights and a plurality of attribute scores, and to store said descriptors, weights and scores in a memory; an assessment element adapted to combine the scores and the weights to yield one or more assessment measures; and an output interface adapted to display said assessment measures.

The tool is preferably implemented as a suitably programmed computer having conventional input/output peripherals including a visual display unit, keyboard and pointing device such as a mouse, and may be provided as software elements on one or more computer readable media or over a data link.

The tool is adapted to aid and improve the assessment of pharmaceutical products by a group of participants having a variety of specialisms. The participants may be lead by a facilitator who organises the assessment exercise.

Preferably, each attribute is allocated to or defined to be in one of a plurality of attribute dimensions. In this way the attributes are grouped into classes to form a hierarchy to assist in the assessment exercise. To use this hierarchy to good effect, each attribute weight preferably defines the weight of the associated attribute within its allocated dimension, and each dimension is also allocated a weight. The assessment element is then preferably adapted to combine the attribute scores with both the attribute weights and the dimension weights to yield said one or more assessment measures.

As a further extension to this hierarchy, the dimensions are preferably grouped into first and second groups, with the dimensions being weighted within each group. The assessment element is then preferably adapted to yield a separate assessment measure for each group. A combined measure could also be derived, using weights for each group measure if required.

In a preferred embodiment, the output interface provides a graph display with a plot of the separate assessment measures for the two groups. Plots of assessment measures arising from parallel assessment scenarios, such as optimistic, pessimistic and neutral pricing scenarios for the same pharmaceutical product may be made on the same graph, for comparison purposes. Pricing position categories may be marked as areas on the graph to assist in visualisation of the results.

To use the hierarchy effectively, the first and second groups of dimensions may be used to separate dimensions and attributes relating firstly to utility aspects, or the clinical performance of the pharmaceutical product being assessed, and secondly to economic aspects, or the willingness of potential purchasers to pay for the product. Dimensions in the first, utility group may include one or more of a clinical safety dimension and a clinical efficacy dimension. Dimensions in the second group may include one or more of an unmet medical need dimension and a cost effectiveness dimension.

The tool is preferably adapted to operate with reference to a comparator product. To this end, the input interface is preferably adapted to accept a comparator product descriptor, with the attribute scores representing ratings of the product being assessed relative to the comparator product. The comparator product descriptor may be, for example, a chemical compound class or name, or a product code.

The tool may further provide an impact analysis interface adapted to list the attribute descriptors ranked by contribution weight to the one or more assessment measures, especially to the group assessment measures derived from the attribute scores and weights and the dimension weights. The contribution weight for an attribute may, for example, be a product of an attribute weight and a dimension weight. This tool may include a graph display as discussed above and a facility to adjust weights and scores and immediately visualise the impact on the assessment measures using new points plotted on the graph.

To this end, the impact analysis interface is preferably adapted to accept revised scores for each attribute and to output revised assessment measures based on the revised scores, for comparison with the original assessment measures, and preferably provides a graphical display of said one or more revised and original assessment measures.

The invention also provides a method of assessing a subject pharmaceutical product relative to a comparator pharmaceutical product, comprising: defining a plurality of product attributes; grouping said attributes into a plurality of attribute dimensions and, for each dimension, associating a relative attribute weight to each attribute grouped therein; grouping said dimensions into a plurality of dimension groups and, for each group, associating a relative dimension weight to each dimension grouped therein; allocating a score to each attribute, said score representing the result of a comparison between said subject product and said comparator product in terms of the associated attribute; and deriving one or more assessment measures from said scores and said weights. This method implements the inventive assessment hierarchy introduced above. Of course, the terms "attribute", "dimension" and "group" are descriptive of logical elements which could be given a variety of other names and have slightly varying functional aspects.

Preferably, a separate assessment measure is derived for each group of dimensions. The dimensions and groups may be constructed along the lines already discussed above. In particular, a first of the groups may comprise dimensions and attributes relating to the clinical performance of said subject and comparator products, and a second of the groups may comprise dimensions and attributes relating to the willingness of potential purchasers to pay for said product.

In a preferred embodiment, the first group comprises one or more of a clinical safety dimension, a clinical efficacy dimension and a quality dimension, while the second group comprises one or more of an unmet medical need dimension, a cost effectiveness dimension and a usefulness dimension.

The method may further comprise the display of results aspects discussed above, including displaying assessment measures corresponding to each of said first and second groups as a point on a graph, and marking on said graph a plurality of regions, each region corresponding to a price position for said subject product relative to said comparator product.

The invention also provides a method of assessing a subject pharmaceutical product comprising: calculating a first group parameter relating to clinical utility of the subject product; calculating a second group parameter relating to economic potential of the subject product; and displaying a price potential of the subject product within a space defined by the first and second group parameters.

Preferably, the first group parameter is calculated from dimension parameters relating to usefulness, unmet medical need and cost effectiveness, and the second group parameter is calculated from dimension parameters relating to quality, efficacy and safety.

The discussed methods are preferably implemented using appropriate data and software process elements on one or more computer systems, and may also be provided by such data and software process elements written into one or more computer readable media or carried over a data link or network.

BRIEF DESCRIPTION OF THE DRAWINGS

Embodiments of the invention will now be described, by way of example, and with reference to the accompanying drawings of which:

FIG. 10 shows the GUI of an impact assessment tool.

PREFERRED EMBODIMENT

The invention is particularly suited for use in an assessment exercise of a subject pharmaceutical product. A suggested exercise involves a number of human participants who are co-ordinated in the exercise by somebody acting as a facilitator. The participants are preferably drawn from a number of different areas of expertise. Through the assessment exercise, the facilitator and the participants together assess the importance of a number of attributes that drive product price and value, thereby providing input for priority setting in market development. The exercise and results thereof help increase objectivity in making pricing decisions, as well as providing a common framework for product assessment across different therapeutic areas. The assessment exercise is carried out with reference to a comparator pharmaceutical product, and yields a price position for the subject product relative to the comparator product.

Figure 1:
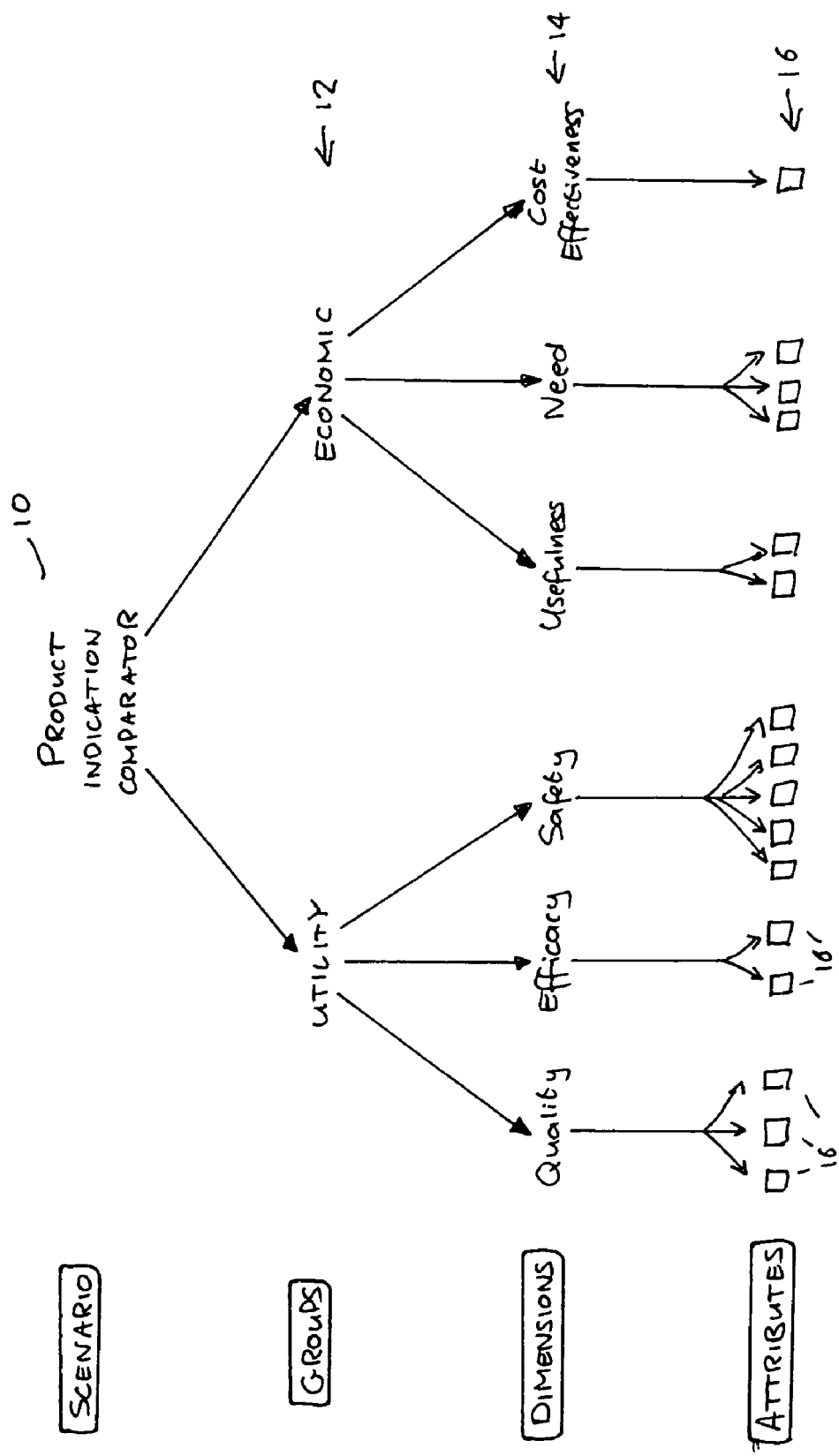
FIG. 1 illustrates a hierarchy of factors for the assessment of a pharmaceutical product.

The subject pharmaceutical product is assessed using a tree of factors which are illustrated in FIG. 1. At the top level of the tree is a single scenario 10 which defines the scope of the assessment exercise in terms of the subject product to be assessed and other factors. At the bottom level of the tree are a plurality of particular attributes 16 on the basis of which the subject product will be assessed. The attributes, which may vary from scenario to scenario, are grouped into six dimensions 14, which are in turn associated into two groups 12. The aim of the assessment exercise is to derive a score for a subject product in each of the two groups, on the basis of the attributes, to thereby derive a price position for the scenario.

The scenario 10 defines the subject pharmaceutical product, a particular clinical area, disease or indication for its use, and a comparator product or therapy. Below the scenario level, the two groups 12 are denoted "product performance", shown in FIG. 1 as "utility", and "willingness to pay", shown in FIG. 1 as "economic". "Product performance" expresses the extent to which relevant medical experts (clinicians, thought leaders, pharmacologists and so on) will value, from a clinical perspective, the subject product relative to other pharmacological therapies and/or non-pharmacological therapies presently used for the same indication.

"Willingness to pay" expresses the degree to which those paying for a product and their advisers (payers), are likely to be prepared to allocate a part of their budget for a particular drug. Willingness to pay is evaluated from a payer's perspective.

Each group 12 in the tree of FIG. 1 is divided into three dimensions 14. The utility group is divided into quality, efficacy and safety dimensions. The economic group is divided into usefulness, need and cost effectiveness dimensions.

The safety dimension covers factors related to a drug's performance in the areas of tolerability, toxicity and contraindications relative to the comparator product, when it is used as recommended for the indication defined in the scenario. The efficacy dimension covers the clinical benefits of the subject product which provide the foundations for claims regarding consistent performance over time when rated against the comparator product. The quality dimension covers product performance characteristics not accounted for in either the efficacy or safety dimensions. Quality factors can be related to various elements including pre-clinical data, mechanism of action, production and pharmacokinetics/pharmacodynamics properties.

The usefulness dimension characterises the ease of use of a product, the likelihood of compliance with government regulations and its capacity to limit the risk of wastage. Usefulness is evaluated from the perspective of patients, providers and payers.

The need dimension relates to the unmet medical need that it is anticipated will be satisfied by the subject product, relative to currently available alternative options, in light of the perceived burdens of the patient, caregivers and society.

The cost effectiveness dimension relates to a product's cost benefit relative to currently available alternative treatment options, for example as defined by outcome based studies. The cost benefit should be evaluated at the price level of the comparator product. Cost effectiveness includes both total budget impact, and affordability from a payer's perspective.

Particular examples of attributes will be provided later in this document, but will often be specific to a particular therapeutic field or indication. A practical number of attributes for each dimension is from about three to six.

Figure 2:
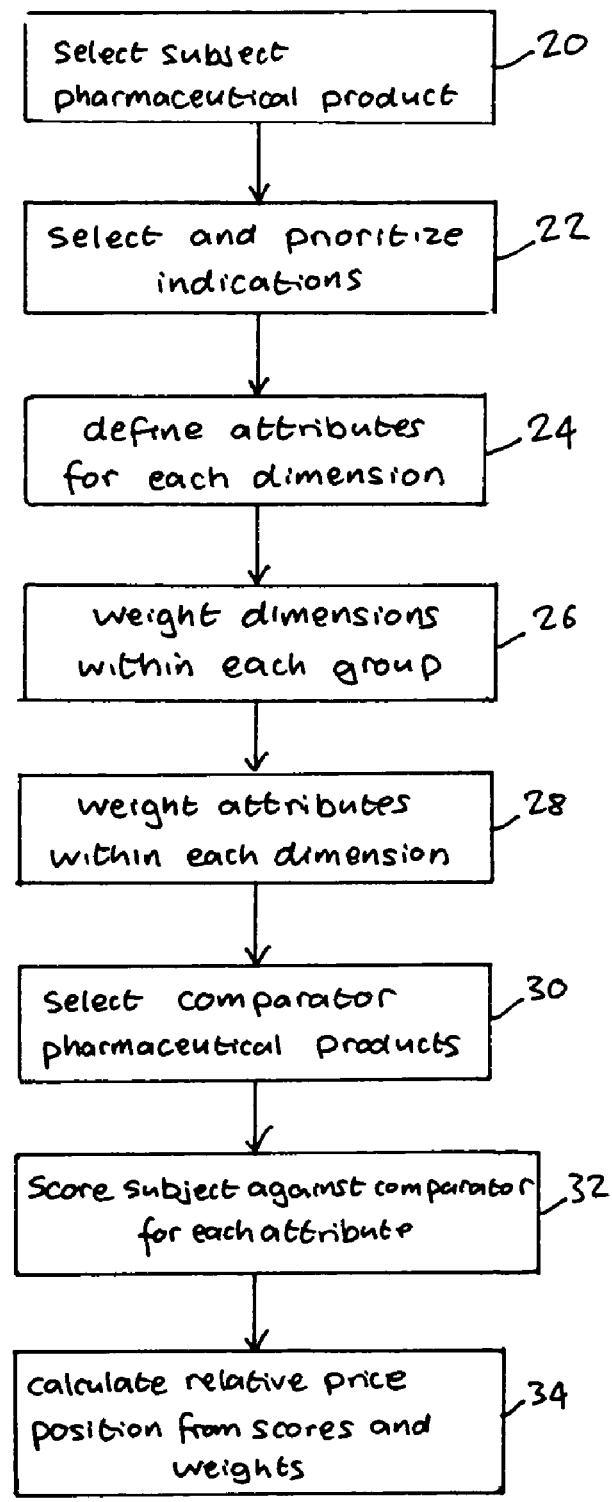
FIG. 2 illustrates a method of making such an assessment using the factors of FIG. 1.

A sequence of stages which may be used by a facilitator and participants or other parties to assess a subject product, in the context of the tree of factors of FIG. 1, is shown in FIG. 2. A particular subject pharmaceutical product for assessment is chosen in step 20. Each product or chemical compound will have one or more therapeutic conditions, or "indications", that it addresses. In step 22 the indications to be studied are selected and prioritised, so that more important indications are assessed first.

Appropriate attributes for each dimension are then defined, in step 24. These attributes may conveniently be based on a template of frequently used attributes, for example for a particular area of therapy or indication. In the following step 26 the weight of each dimension in each group is set by the participants and facilitator. These weights may be expressed as percentages so that, for example, the quality, efficacy and safety dimensions could have weights of 30%, 30% and 40% for a particular scenario. The weighting of the dimensions should be carried out from the perspective of clinicians and payers, to represent the importance that these parties would assign to each dimension.

The weight of each attribute within each dimension is then selected by the participants and facilitator, in step 28. Again, this weighting should be carried out from the perspective of clinicians and payers, to represent the importance that these parties would assign to each attribute.

The scenario for the assessment is further defined in step 30 in which one or more comparator pharmaceutical products are selected. Suitable comparator products may be products, including drugs or treatments, which are considered by clinicians and payers to be gold standards for a particular indication. Products which are current price or market leaders for the indication, or products which rely on the same active ingredient as the subject product may also make suitable comparator products. The selection of an appropriate comparator product is very important, as the comparator serves as a point of reference for assessing the subject product. Comparator selection may be country specific, for example because of national laws.

Having determined the scenario, the attributes to be used, and the weights of the attributes and dimensions, the next step 32 is to score the subject product against the or each comparator product, for each attribute. The weights and scores are then used in step 34 to calculate result values for the utility and economic groups, from which a price position of the subject product relative to the target product is derived and displayed.

Figure 3:
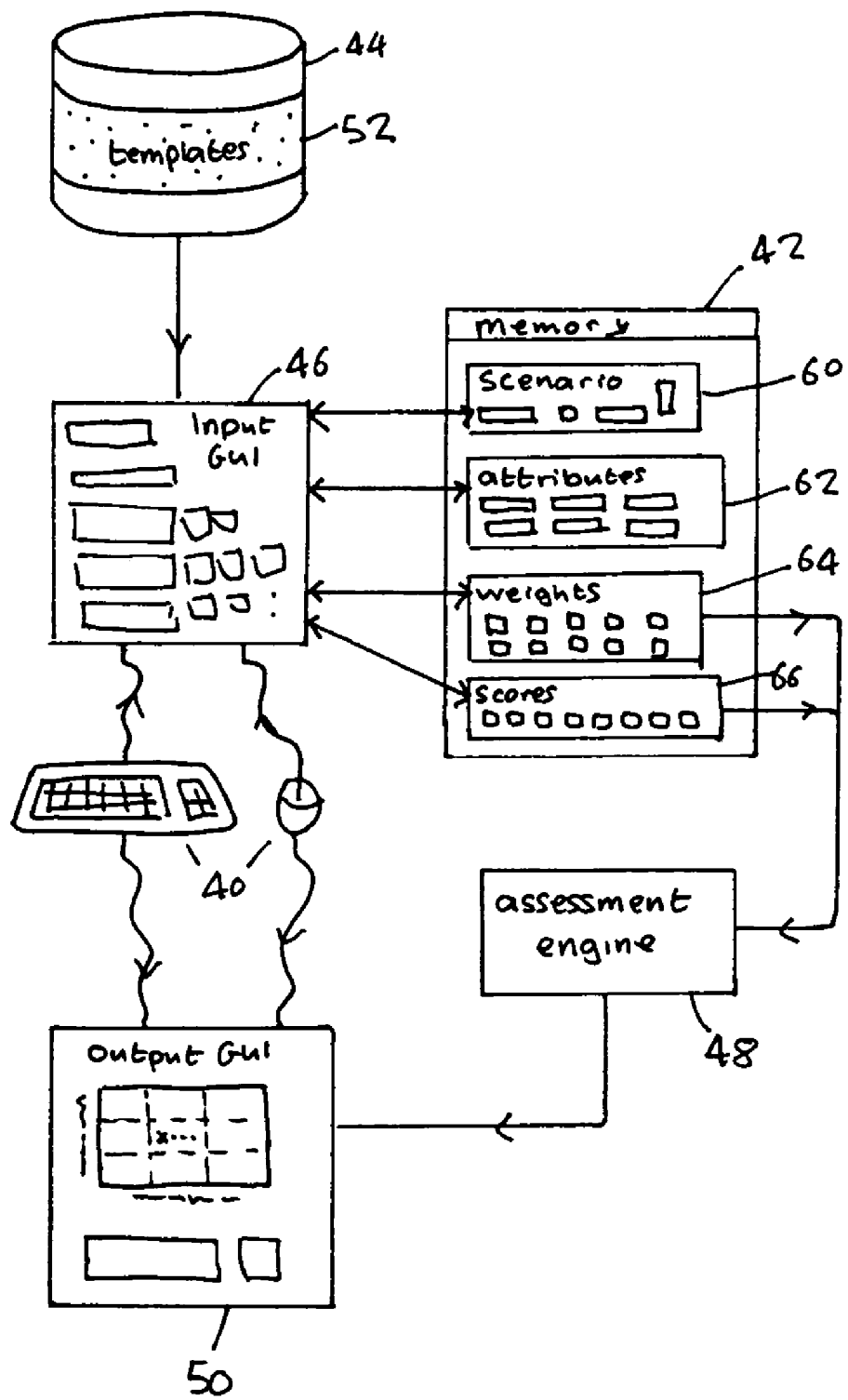
FIG. 3 is a schematic of apparatus for putting the method of FIG. 2 into effect.

A tool for assisting in the above described assessment exercise is illustrated in FIG. 3. The tool is provided by a computer system having conventional input devices 40 such as a mouse and keyboard, volatile memory 42 and non volatile memory 44 linked to a central processing unit (not illustrated). The input devices and a visual display unit are used to provide an input graphical user interface or GUI (46) by means of which data items are entered into the memory 42. These data items are subsequently processed by a software implemented assessment engine (48) and the results of the processing presented using an output GUI (50).

The non volatile memory 44, which could be provided by a magnetic disk drive, contains one or more templates 52 for providing default or template parameters to the input GUI 46. Such parameters may include product attributes, and attribute and dimension weights for particular therapeutic areas or classes of drugs, to assist in the preparation of attributes and weights for a particular scenario. Templates may also provide template parameters defining scenarios.

As a result of parameters passed to the input GUI 46 from templates 52 and input directly into the input GUI 46 by the facilitator and participants using the input devices 40, the various assessment parameters are stored in the volatile memory 42, including scenario parameters 60, attributes 62, weights 64 and scores 66. If multiple scenarios are being assessed at the same time, for example using multiple indications or comparators for one subject pharmaceutical product, then multiple sets of parameters, especially scores, may be stored at the same time.

Figure 4:
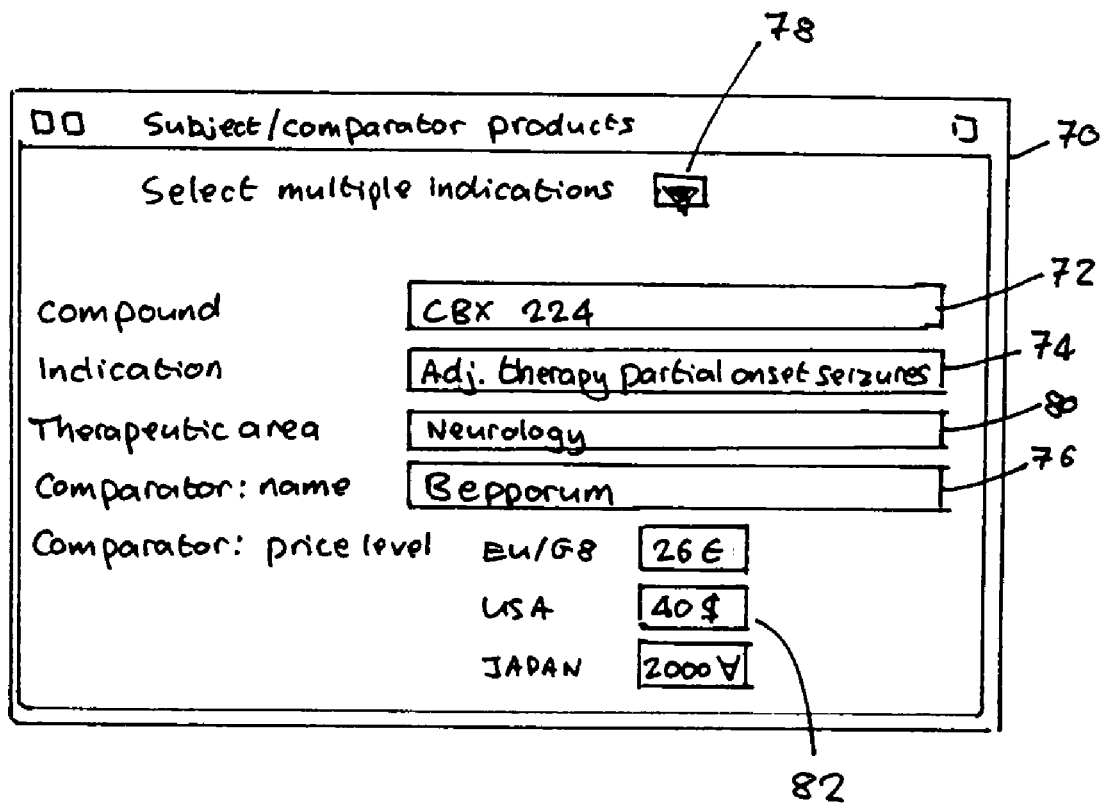
FIG. 4 shows a scenario input window of the input graphical user interface (GUI) of FIG. 3.

In FIG. 4 there is illustrated a scenario entry window 70 of the input GUI 46 for entering scenario data. The window allows the user to enter the name of the subject pharmaceutical product 72, the medical indication 74 and the name of the comparator product 76. Multiple different indications for the same subject product can be entered by using the select multiple indication control 78. The therapeutic area 80 under consideration and comparator price levels 82 may also be entered. In the present example, the indication is partial onset seizures in the general therapeutic area of neurology.

Figure 5:
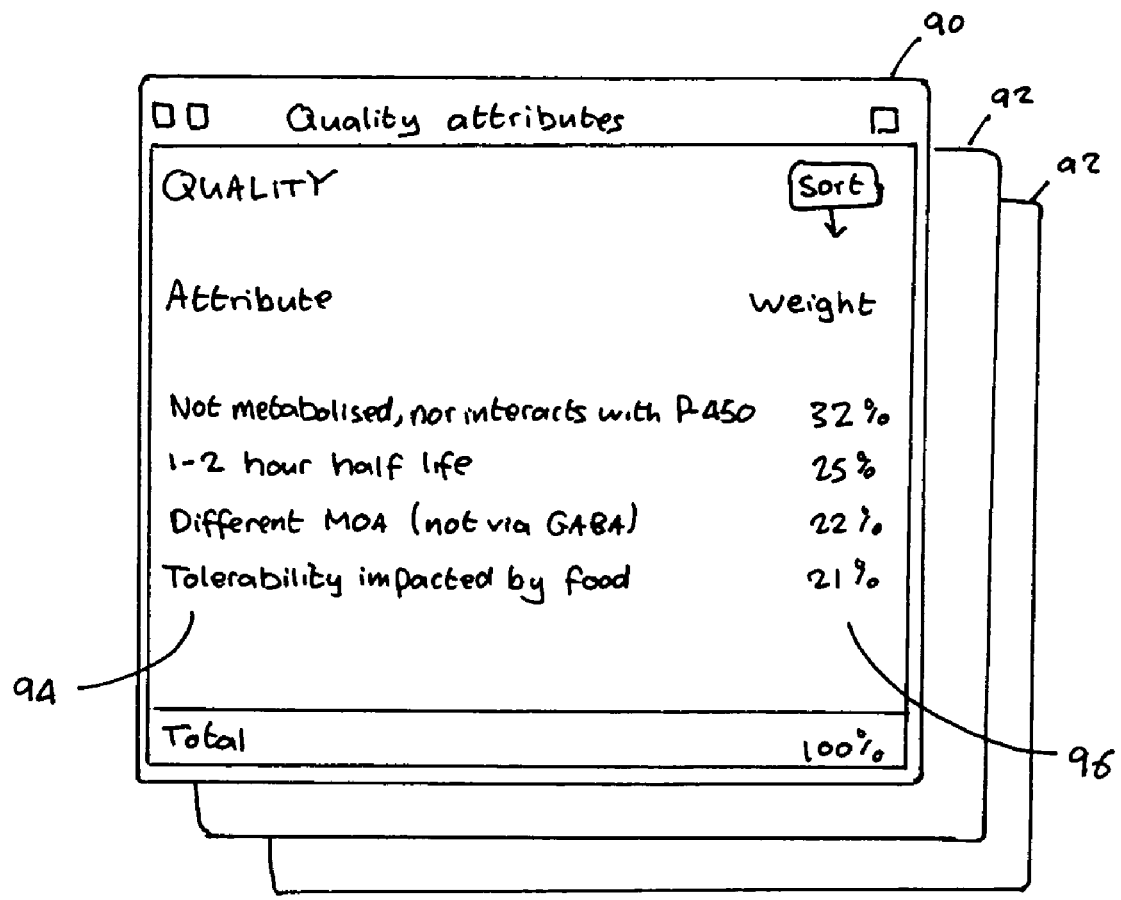
FIG. 5 shows an attribute input window of the input GUI of FIG. 3.

In FIG. 5 there is shown an attribute entry window 90 of the input GUI 46. The illustrated window 90 is used to enter attributes belonging to the quality dimension, and weights for each of these attributes. Further attribute entry windows 92 are used to enter attributes belonging to other dimensions. An initial set of attributes 94 and attribute weights 96 may be taken from a template 52, and then edited by the user, or entered in their entirety using the attribute entry window 90. It will be seen that the weights 96 shown in the window add up to 100%.

Figure 6:
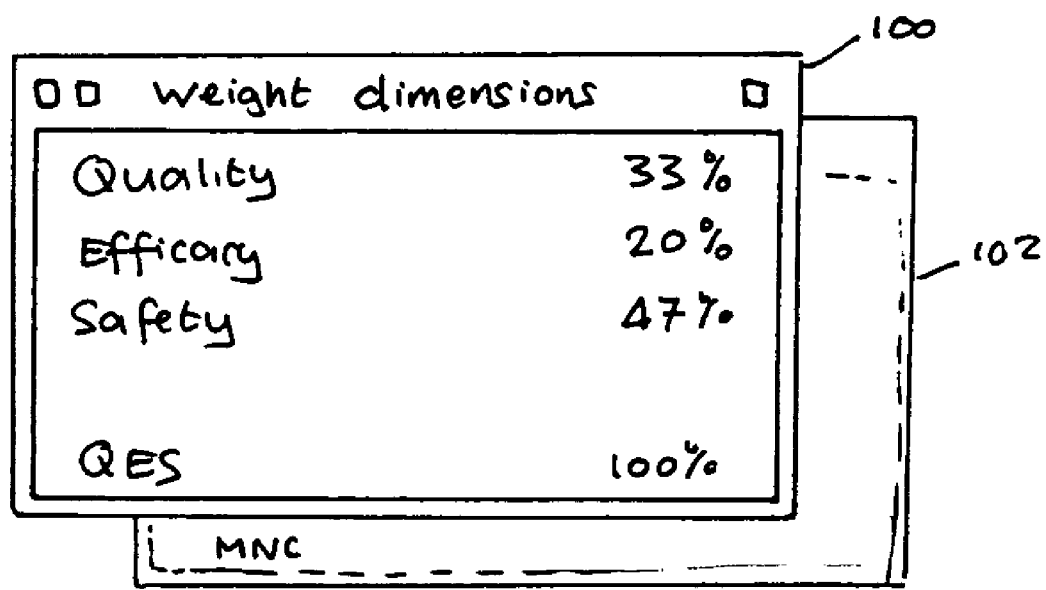
FIG. 6 shows a dimension weight input window of the input GUI of FIG. 3.

Referring now to FIG. 6 there is shown a dimension weight entry window 100 of the input GUI 46. The illustrated window allows entry of weights for each of the quality, efficacy and safety dimensions. A further dimension weight entry window 102 allows entry of weights for each of the usefulness, need and cost effectiveness dimensions.

Figure 7:
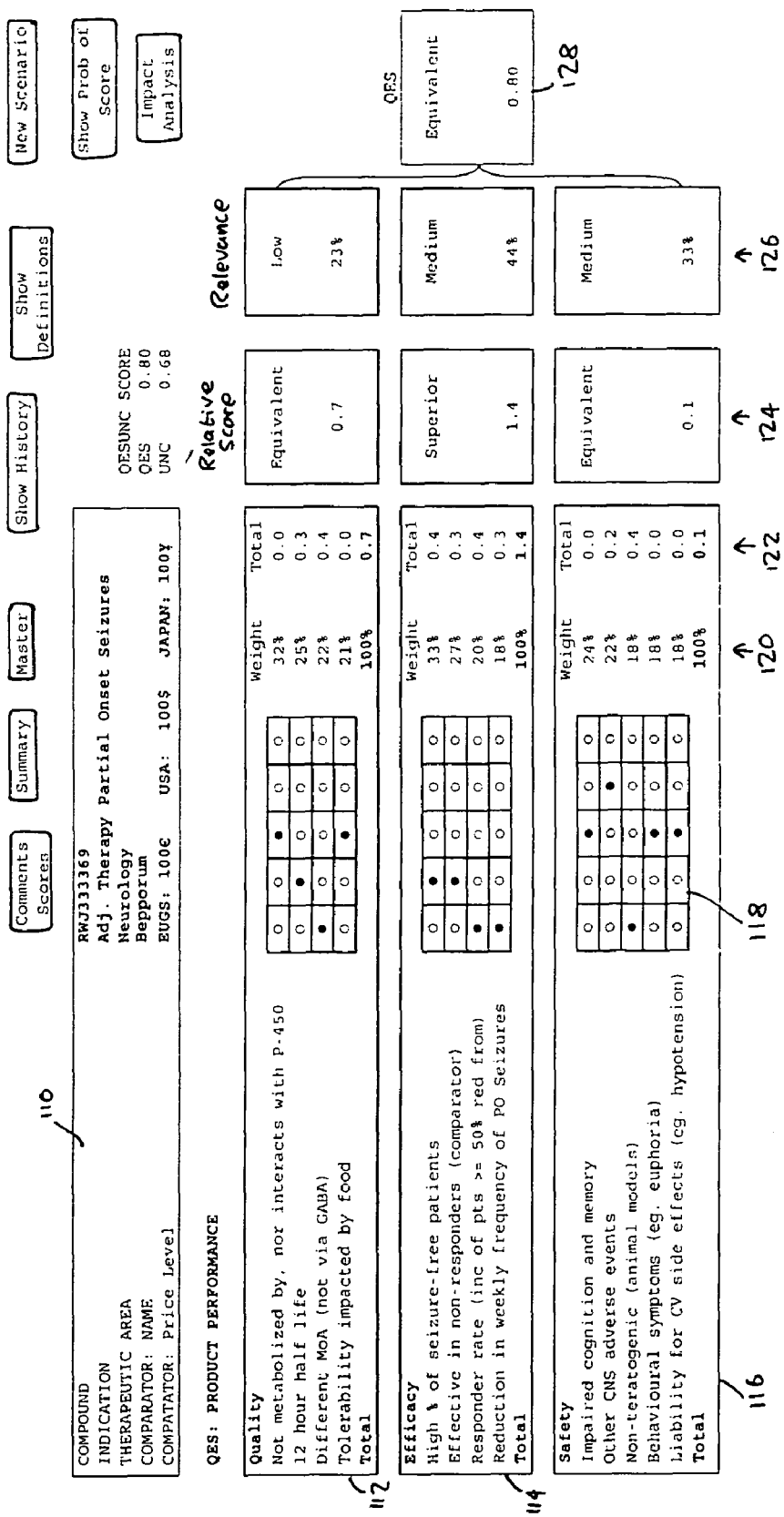
FIG. 7 shows an upper part of a scoring window of the input GUI.
Figure 8:
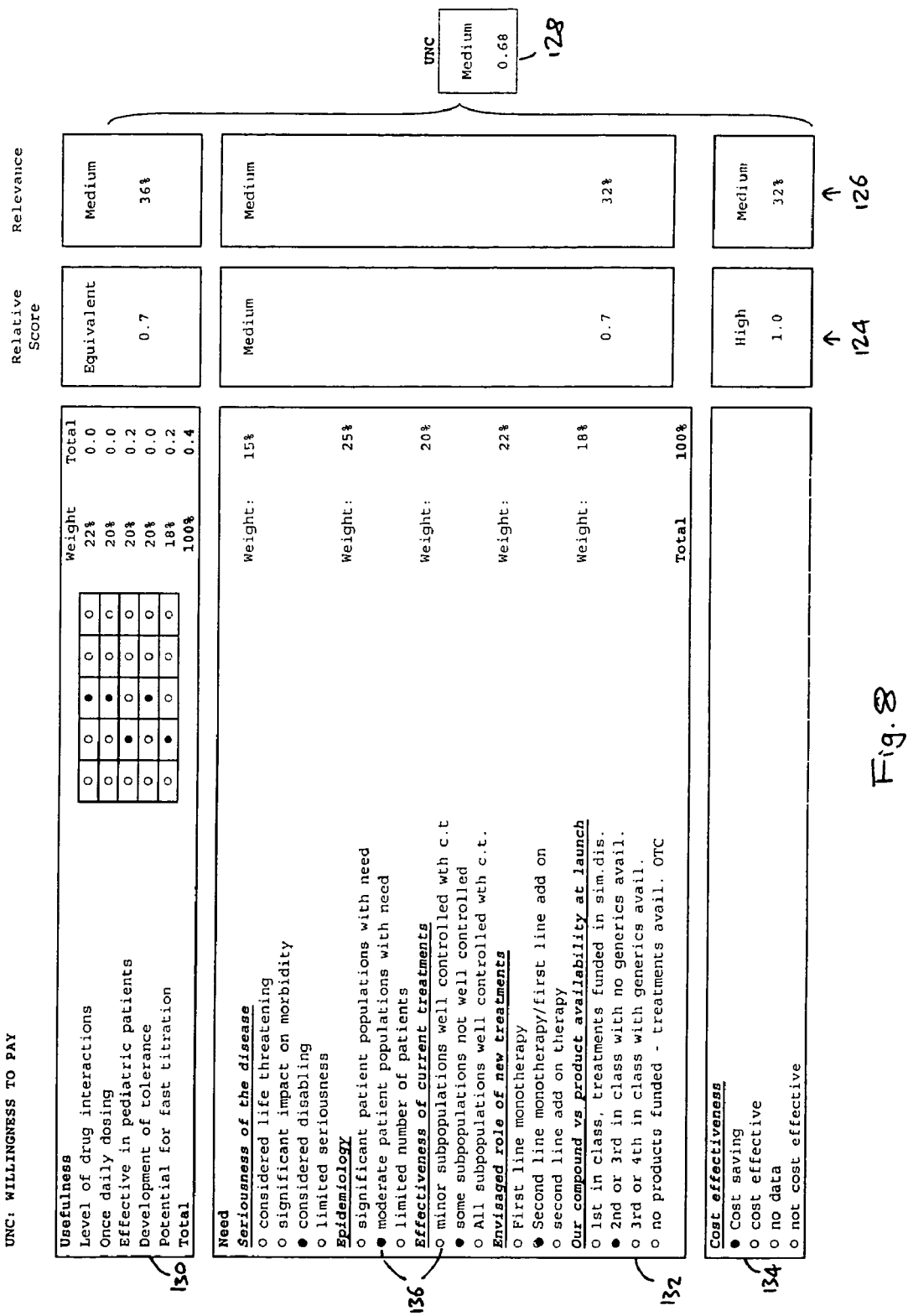
FIG. 8 shows a lower part of a scoring window of the input GUI.

FIG. 7 shows an upper portion of a scoring window provided by the input GUI 46. The corresponding lower portion is shown in FIG. 8. Details of the scenario are set out in a scenario box 110. Below the scenario box 110 are dimension scoring boxes, 112, 114, 116 for each of the quality, efficacy and safety dimensions. In each dimension scoring box the attributes for that dimension are listed. Alongside each attribute is a row of score buttons 118. By selecting one of the score buttons alongside an attribute a score for that attribute is recorded. Next to the score buttons, the defined weight 120 for each attribute is displayed and then a total column 122 combining the attribute score and weight into a single number.

Alongside each dimension scoring box is a relative score box 124 and a relevance box 126. The relative score box contains a relative score number which is the sum of the numbers in the total column of the corresponding dimension scoring box. A number of text labels are pre-allocated to sub-ranges within which the relative score number can fall, and the appropriate text label is also displayed in the relative score box 124.

Each relevance box 126 displays the weight allocated to the corresponding dimension. A number of text labels are pre-allocated to sub-ranges within which the relevant dimension weight can fall, and the appropriate text label is also displayed in the relevance box 126.

Finally, a single group score box 128 is shown alongside the three relevance boxes 126. The group score, calculated from the score and weight for each dimension, is displayed along with a text label, as for the relevance and dimension scoring boxes.

The score buttons 118 in the dimension scoring boxes allow the users to select one of five scores. Each score has an associated numerical value. The scores are as follows:

Significantly superior to the comparator=+2;
Superior to the comparator=+1;
Equivalent to the comparator=0;
Inferior to the comparator=−1;
Significantly inferior to the comparator=−2.

A subject product is significantly superior when its performance pertaining to the attribute in question represents a major improvement over the comparator product, and will be perceived as such by payers. A major improvement is preferably to be confirmed in a randomized clinical trial. A product is superior when its performance represents a clear improvement over the comparator. If there is no improvement, but the subject product is not worse than the comparator then the product is equivalent, whereas if the performance of the product is somewhat worse than that of the comparator, the product should be scored as inferior. The significantly inferior score should only be used if the performance of the subject product is considerably worse then that of the comparator in respect of the attribute in question.

Suitable textual labels for the relative score boxes 124 are "superior", "equivalent", and "inferior" corresponding to relative score ranges of −2 to −0.6; −0.6 to +0.6; and +0.6 to +2.0, suitable textual labels for the relevance boxes 126 are "low", "medium" and "high", corresponding to dimension weights of 0% to 30%, 30% to 70%; and 70% to 100%. The same textual labels and ranges may be used for the group score box 128 as for the relative-score boxes 124.

The totals for each attribute displayed in the total column 122 may be derived by a simple arithmetic weighting of each score. The relative score shown in each relative score box 124 may be a simple sum of the attribute totals for that dimension. The group score shown in the group score box may be a simple sum of the relative scores weighted by the dimension relevance values.

FIG. 8 shows a lower portion of a scoring window provided by the input GUI 46. The corresponding upper portion is shown in FIG. 7. As in FIG. 7, there are three dimension scoring boxes. These dimension scoring boxes relate to the usefulness, need and cost effectiveness dimensions, and also have associated relative score boxes 124, relevance boxes 126 and a single group score box 128. The usefulness dimension scoring box 130 is essentially the same as the quality, efficacy and safety scoring boxes of FIG. 7, apart from containing a different list of attributes.

The need dimension scoring box 132 contains five standard attributes, each having three or four need score buttons 136, rather than the five standard score buttons used for each of the quality, efficacy, safety and usefulness attributes. The five standard attributes for the need dimension are "seriousness of the disease", "epidemiology", "effectiveness of current treatments", "envisaged role of new treatment" and "our compound vs product availability at launch and/or evaluation" Different sets of standard "need" attributes and scoring options for different scenarios or therapeutic areas may be provided, for example for cancer and non-cancer areas.

The cost effectiveness dimension box 134 contains a single attribute of "cost effectiveness per patient", with four score buttons labelled as "cost saving", "cost effective", "no data" and "not cost effective". Of course, one or more different attributes and scoring schemes may be used for this dimension, and indeed any of the other dimensions.

The textual labels used in the relative score boxes and group score box of FIG. 8 are "low", "medium" and "high", rather than "inferior", "equivalent" and "superior" as used in FIG. 7, but the same or similar range boundaries may be used.

Figure 9:
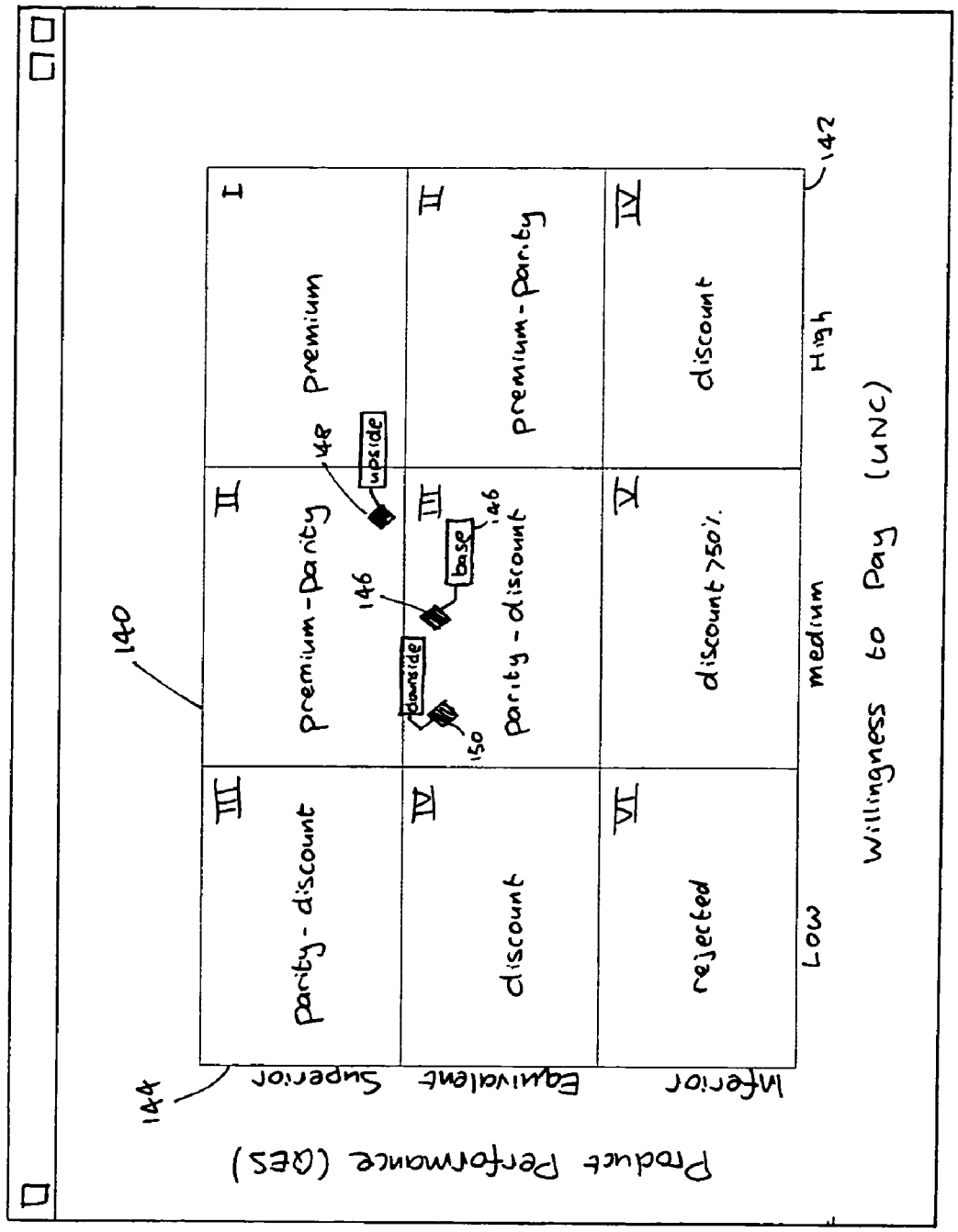
FIG. 9 shows a graph display of the output GUI of FIG. 3.

Following entry of scores for each attribute, the data gathered may be displayed using a window as the output GUI 50 such as the window illustrated in FIG. 9. In the window, a price position graph 140 has horizontal and vertical axes labelled "willingness to pay (UNC)" 142 and "product performance (QES)" 144. On this price position graph is plotted a base point 146 at a graph position determined by the values displayed in the group score boxes 128 of FIGS. 7 and 8. The graph area is divided into nine boxes by lines or colour changes defined by the same numerical boundaries used to define the "high", "medium" and "low" ranges and the "superior", "equivalent" and "inferior" ranges of the group scores discussed above, with appropriate textual labels being used on the axes.

Each of the nine boxes is associated with a price position category. These categories are adapted from the French ASMR pharmaceutical evaluation model, and may include suitable pricing premiums or discounts, in percentage terms, relative to the market price of the comparator product. The price position categories used in FIG. 9 are:

I. premium; >+20%
II. premium—parity; 0% to 20%
III. parity—discount; −20% to 0%
IV. discount; −50% to −20%
V. discount; <−50%
VI. rejected In addition to a base point 146, the results of two other assessment exercises are plotted on the graph 140. An "upside" point 148 results for a repeat assessment using the same basic scenario factors and attributes, but with a more optimistic set of scores. A "downside" point 150 similarly results from a repeat exercise with a less optimistic set of scores. Other parallel assessments may be made to investigate different eventualities as required.

FIG. 10 illustrates a further window of the output GUI 50. This window provides one or more impact analysis tables 150, 152. In FIG. 10 there is such a table 150 listing all of the utility group attributes and a table 152 listing all of the economic group attributes. Alongside each attribute is listed its weight 154 within the associated dimension, the relevance weight 156 of the associated dimension within the group, and an impact value 158 which is the product of the weight and relevance values. The attributes in each table 150, 152 are ordered according to impact value. These tables are very helpful in identifying the impact of different attributes on the group scores are derived price position plotted in FIG. 9.

The impact analysis tables 150, 152 also include original score columns 160 and new score columns 162, for one or more different assessments. The original sore columns contain the attribute scores entered using the score table of FIGS. 7 and 8. The new score columns initially contain the same scores, but are editable. An associated price position graph 164, similar to the graph of FIG. 9, plots the group scores resulting from both the original score columns and the new score columns, so that the impact on price position of changing one or more of the scores in the new score columns 162 can immediately be seen.

The slightly varying scenarios represented by the multiple columns of both the original score and the new score column groups 160, 162 are listed, for convenience, in a scenario names box 166.

A further window of the output GUI 50 provides a "probability of score" tool. The degree of uncertainty in the score for each attribute is controllable, for example by selecting one of several pre-defined confidence ranges associated with text labels such as "low", "medium" and "high". These degrees of uncertainty are combined to determine a degree of uncertainty in each of the group scores. These degrees of uncertainty are plotted as error bars in each of the two dimensions of a price position plot similar to that of FIG. 9.

Although particular embodiments have been described, a number of variations and alternatives will be apparent to the skilled person without departing from the spirit and scope of the invention.

The invention claimed is:

1. Apparatus for assisting in the assessment of a pharmaceutical product, comprising:
a memory, the memory having stored thereon: a plurality of attribute descriptors relating to attributes of the product to be assessed; a plurality of attribute weights; a plurality of dimension weights; and a plurality of attribute scores, each of said attribute scores representing a respective result of a comparison between said pharmaceutical product and a comparator product in terms of the associated attribute; and
a central processing unit linked to the memory, the central processing unit configured to:
provide an input interface to accept:
a comparative product descriptor;
said attribute descriptors, attribute weights, dimension weights, and attribute scores;
an allocation of each attribute into one of a plurality of dimensions, each attribute weight defining a relative weight of the associated attribute within the dimension to which that attribute is allocated; and
an allocation of each dimension into one of a plurality of dimension groups, each dimension weight defining a relative weight of the associated dimension within the dimension group to which that dimension is allocated;
calculate:
a weighted score for each of said attributes;
a plurality of total attribute dimension scores by calculating the sum of the weighted scores for each of said attributes in each of the plurality of attribute dimensions;
a plurality of total dimension scores by calculating the sum of the product of the plurality of total attribute dimension scores weighted by dimension group weight for each of said dimension groups;
provide an assessment element adapted to derive one or more assessment measures from said scores; and
provide an output interface adapted to display said one or more assessment measures.

2. The apparatus of claim 1 wherein the assessment element yields a separate assessment measure for each group.

3. The apparatus of claim 2 wherein a first one of said groups comprises dimensions and attributes relating to the clinical performance of said product, and a second one of said groups comprises dimensions and attributes relating to the willingness of potential purchasers to pay for said product.

4. The apparatus of claim 1 wherein said dimensions include one or more of a clinical safety dimension and a clinical efficacy dimension, an unmet medical need dimension and a cost effectiveness dimension.

5. The apparatus of claim 1 wherein the central processing unit further provides an impact analysis interface adapted to list the attribute descriptors ranked by contribution weight to the one or more assessment measures.

6. The apparatus of claim 5 wherein said impact analysis interface is adapted to accept revised scores for each attribute and to output revised assessment measures based on the revised scores, for comparison with the original assessment measures.

7. The apparatus of claim 6 wherein the impact analysis interface provides a graphical display of said one or more revised and original assessment measures.

8. The apparatus of claim 1, wherein the central processing unit is further configured to use the one or more assessment measures to derive a price position of said pharmaceutical product relative to said comparator product.

9. A method of assessing a subject pharmaceutical product relative to a comparator pharmaceutical product, comprising:
defining, by a computer, at least one comparator scenario including:
defining a plurality of product attributes;
grouping said product attributes into a plurality of attribute dimensions and, for each of the plurality of attribute dimensions, assigning a relative attribute dimension weight to each of said product attributes grouped therein;

grouping said plurality of attribute dimensions into a plurality of dimension groups and, for each group, assigning a relative dimension weight to each of the plurality of dimensions grouped therein;

assigning, via the computer, a score to each of said attributes representing the result of a comparison between said subject product and said comparator product in terms of the associated attribute;

calculating, via the computer,
- a weighted score for each of said attributes;
- a plurality of total attribute dimension scores by calculating the sum of the weighted scores for each of said attributes in each of the plurality of attribute dimensions;
- a plurality of total dimension scores by calculating the sum of the product of the plurality of total attribute dimension scores weighted by dimension group weight for each of said dimension groups; and deriving one or more assessment measures from said scores.

10. The method of claim 9 wherein a separate assessment measure is derived for each dimension group.

11. The method of claim 9 wherein a first of said groups comprises dimensions and attributes relating to the clinical performance of said subject and comparator products, and a second of said groups comprises dimensions and attributes relating to the willingness of potential purchasers to pay for said product.

12. The method of claim 11 wherein said first group comprises one or more of a clinical safety dimension, a clinical efficacy dimension and a quality dimension.

13. The method of claim 11 wherein said second group comprises one or more of an unmet medical need dimension, a cost effectiveness dimension and a usefulness dimension.

14. The method of claim 11 further comprising displaying assessment measures corresponding to each of said first and second groups as a point on a graph.

15. The method of claim 14 further comprising marking on said graph a plurality of regions, each region corresponding to a price position for said subject product relative to said comparator product.

16. The method of claim 9, further comprising using the one or more assessment measures to derive a price position of the subject pharmaceutical product relative to the comparator pharmaceutical product.

* * * * *